United States Patent [19]

Poss

[11] Patent Number: 5,466,704
[45] Date of Patent: Nov. 14, 1995

[54] N-SUBSTITUTED IMIDAZOLE AND BENZIMIDAZOLE DERIVATIVES USEFUL AS ANGIOTENSON II ANTAGONISTS

[75] Inventor: Michael A. Poss, Lawrenceville, N.J.

[73] Assignee: E. R. Squibb & Sons, Inc., Princeton, N.J.

[21] Appl. No.: 263,582

[22] Filed: Jun. 22, 1994

Related U.S. Application Data

[63] Continuation of Ser. No. 847,381, Mar. 6, 1992, abandoned, which is a continuation-in-part of Ser. No. 661,288, Feb. 16, 1991, abandoned.

[51] Int. Cl.$^6$ .......................... A61K 3/41; A61K 31/415; A61K 31/50; C07D 487/04; C07D 471; C07D 04; C07D 497/12
[52] U.S. Cl. .......................... 514/381; 514/397; 548/252; 548/253; 548/306.1; 548/314.7
[58] Field of Search .......................... 548/306.1, 314.7, 548/252, 253; 514/397, 381

[56] References Cited

U.S. PATENT DOCUMENTS

| | | | |
|---|---|---|---|
| 4,328,348 | 5/1982 | Ogata et al. | 548/314.7 X |
| 4,463,011 | 7/1984 | Ogatha et al. | 548/314.7 X |
| 4,582,837 | 4/1986 | Hauel et al. | 548/306.1 X |
| 4,859,684 | 8/1989 | Raeymakers et al. | 548/306.1 X |
| 5,177,074 | 1/1993 | Allen et al. | 548/306.1 X |
| 5,177,097 | 1/1993 | Poss | 548/314.7 X |
| 5,180,724 | 1/1993 | Bowles et al. | 548/306.1 X |
| 5,190,942 | 3/1993 | Poss | 548/306.1 X |
| 5,200,412 | 4/1993 | Whittaker et al. | 548/306.1 X |

FOREIGN PATENT DOCUMENTS

| | | | |
|---|---|---|---|
| 0200322 | 3/1986 | European Pat. Off. | 548/314.7 |
| 91-06454 | 5/1991 | WIPO | 548/314.7 |

*Primary Examiner*—Floyd D. Higel
*Attorney, Agent, or Firm*—Theodore R. Furman, Jr.; Ellen K. Park

[57] ABSTRACT

Compounds are disclosed having the formula

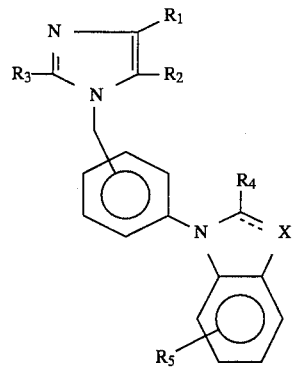

These compounds inhibit the action of angiotensin II and are useful, therefore, for example, as antihypertensive agents.

12 Claims, No Drawings

N-SUBSTITUTED IMIDAZOLE AND BENZIMIDAZOLE DERIVATIVES USEFUL AS ANGIOTENSON II ANTAGONISTS

This is a continuation of application Ser. No. 07/847,381, filed Mar. 6, 1992, now abandoned, which is a continuation-in-part of application Ser. No. 07/661,288, filed Feb. 16, 1991, now abandoned.

FIELD OF THE INVENTION

The present invention relates to novel substituted imidazoles which are useful as antihypertensive agents.

SUMMARY OF THE INVENTION

In accordance with the present invention, novel compounds which inhibit the action of the hormone angiotensin II are disclosed. These compounds are of the general formula

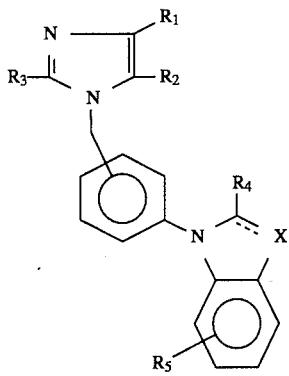

and pharmaceutically acceptable salts thereof;
where X can be —N— or

when X=N, the double bond is always present;
$R_1$ is hydrogen, halogen, —$NO_2$, —$CF_3$ or —CN;
$R_2$ is H, CN alkyl of 1 to 10 carbon atoms, alkenyl of 3 to 10 carbon atoms, or the same groups substituted with F; phenylalkenyl wherein the aliphatic portion is 2 to 6 carbon atoms; —$(CH_2)_m$-imidazol-1-yl; —$(CH_2)_m$-1,2,3-triazolyl optionally substituted with one or two groups selected from $COOR_7$ or alkyl of 1 to 4 carbon atoms;

—$(CH_2)_m$-tetrazolyl; —$(CH_2)_n OR_6$; —$(CH_2)_n OCR_7$;

—$(CH_2)_n SR_8$; —CH=CH$(CH_2)_s$CHOR$_8$;

—CH=CH$(CH_2)_s$CR$_9$; —CR$_9$; —CH=CH$(CH_2)_s$OCR$_6$;

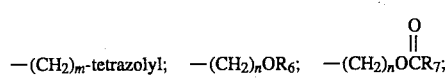

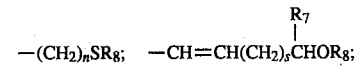

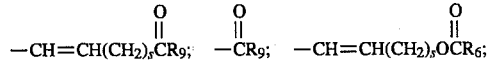

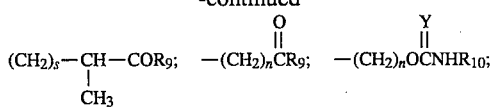

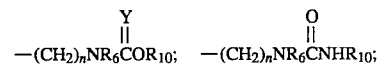

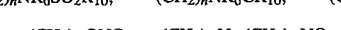

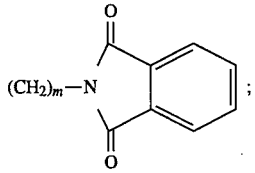

or $R_1$ and $R_2$ taken together with the carbon atoms of the imidazole nucleus to which they are attached can form a benzimidazole shown as

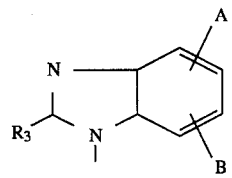

wherein A can be hydrogen, alkyl, $C_xF_{2x+1}$, $C_6F_5$, halogen, $C_{1-6}$ alkoxy, —$(CH_2)_x$OH, —$(CH_2)_x$—$OC_{1-4}$alkyl,

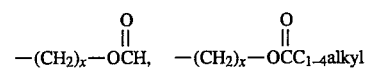

or —COR$_9$ and B can be hydrogen, alkyl, $C_xF_{2x+1}$, $C_6F_5$, halogen or $C_{1-6}$alkoxy;
$R_3$ is alkyl of 2 to 10 carbon atoms, alkenyl or alkynyl of 3 to 10 carbon atoms or the same groups substituted with F or $CO_2R_7$; cycloalkyl of 3 to 8 carbon atoms, cycloalkylalkyl of 4 to 10 carbon atoms; cycloalkylalkenyl or cycloalkylalkynyl of 5 to 10 carbon atoms; $(CH_2)_xZ(CH_2)_mR'$ (wherein R' is H, $C_{1-6}$ alkyl, $C_{3-6}$cycloalkyl, $C_{2-4}$alkenyl or $C_{2-4}$alkynyl) optionally substituted with F or $CO_2R_7$; benzyl or benzyl substituted on the phenyl ring with 1 or 2 halogens, alkoxy of 1 to 4 carbon atoms, alkyl of 1 to 4 carbon atoms or nitro;
$R_4$ and $R_4'$ are independently selected from hydrogen, alkyl, aryl, cycloalkyl, aralkyl, —$COOR_7$,

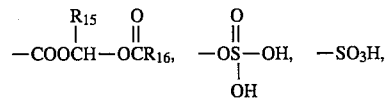

-continued

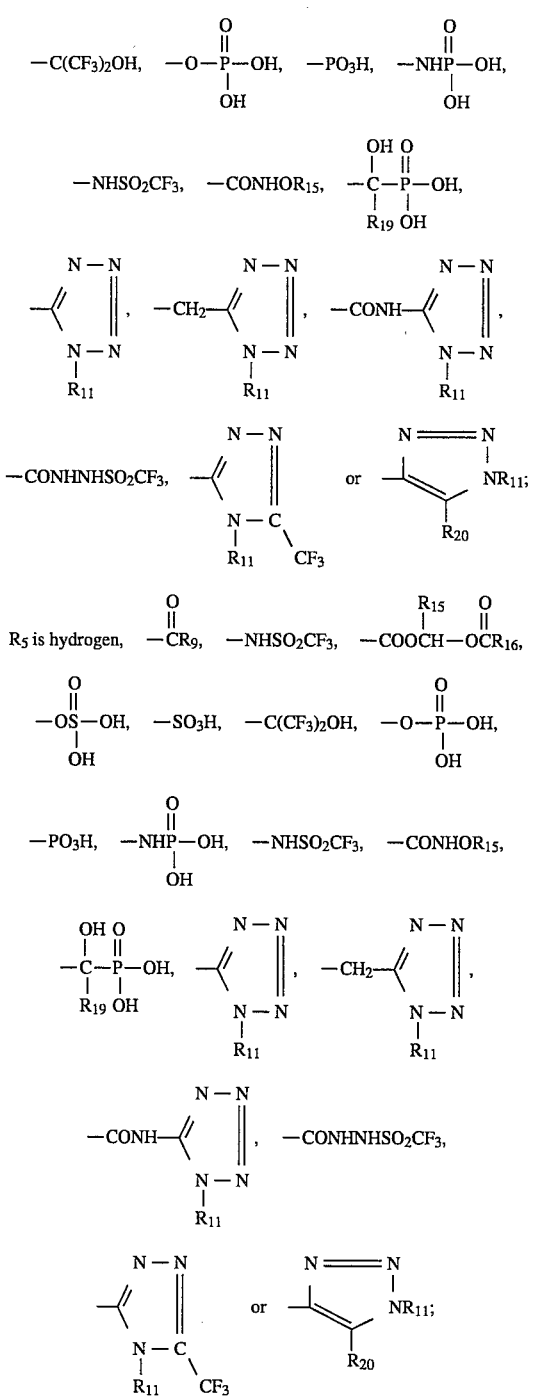

$R_6$ is H, alkyl of 1 to 6 carbon atoms, cycloalkyl of 3 to 6 carbon atoms, phenyl or benzyl;

$R_7$ is H, alkyl or perfluoroalkyl of 1 to 8 carbon atoms, cycloalkyl of 3 to 6 carbon atoms, phenyl or benzyl;

$R_8$ is H, alkyl of 1 to 6 carbon atoms, cycloalkyl of 3 to 6 carbon atoms, phenyl, benzyl, acyl of 1 to 4 carbon atoms, phenacyl;

$R_9$ is H, alkyl of 1 to 6 carbon atoms, cycloalkyl of 3 to 6 carbon atoms, $(CH_2)_pC_6H_5$, $OR_{11}$ or $NR_{12}R_{13}$;

$R_{10}$ is alkyl of 1 to 6 carbon atoms or perfluoroalkyl of 1 to 6 carbon atoms, 1-adamantyl, 1-naphthyl, 1-(1-naphthyl) ethyl, or $(CH_2)_pC_6H_5$;

$R_{11}$ is H, alkyl of 1 to 6 carbon atoms, cycloalkyl of 3 to 6 carbon atoms, aryl, arylalkyl, a 5- to 7-membered carbocyclic ring which may have another 5- to 7-membered carbocyclic ring fused thereto,

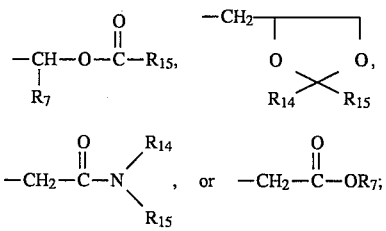

$R_{12}$ and $R_{13}$ independently are H, alkyl of 1 to 4 carbon atoms, phenyl, benzyl, α-methylbenzyl, or taken together form a ring of the formula

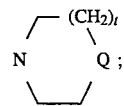

Q is $NR_{14}$, O or $CH_2$;

$R_{14}$ and $R_{15}$ are independently H, alkyl, aryl, aralkyl or cycloalkyl;

$R_{16}$ is $C_{1-6}$alkyl, $-NR_{17}R_{18}$ or

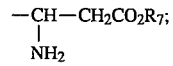

$R_{17}$ and $R_{18}$ are independently H, $C_{1-6}$alkyl, benzyl or taken together are 3 to 6 carbon atoms forming a 4- to 7-membered ring with the nitrogen atom to which they are attached;

$R_{19}$ is H, $C_{1-5}$alkyl, phenyl;

$R_{20}$ is $-CN$, $-NO_2$ or $-CO_2R_7$;

Y=O or S;

Z=O, $NR_6$ or S;

m is 1–5;

n is 1–10;

p is 0–3;

q is 2–3;

r is 0–2;

s is 0–5;

t is 0 or 1; and x is 1 to 6.

DETAILED DESCRIPTION OF THE INVENTION

In its broadest aspects the present invention relates to the compounds of formula I and to pharmaceutical compositions and methods employing such compounds.

The term "aryl", as used throughout the specification either by itself or as part of a larger group, refers to phenyl or phenyl substituted with halogen, alkyl, alkoxy, alkylthio, hydroxy, alkanoyl, nitro, amino, dialkylamino, or trifluoromethyl groups. Phenyl and monosubstituted phenyl are preferred and phenyl is the most preferred.

The term "alkyl", as used throughout the specification either by itself or as part of a larger group, refers to groups having 1 to 10 carbon atoms. Alkyl groups having 1 to 4 carbon atoms are preferred.

The term "cycloalkyl", as used throughout the specification either by itself or as part of a larger group, refers to groups having 3 to 7 carbon atoms.

The term "alkoxy", as used throughout the specification either by itself or as part of a larger group, refers to groups having 1 to 8 carbon atoms. Alkoxy groups having 1 to 3 carbon atoms are preferred.

The term "halogen", as used by itself or as part of a larger group refers to fluorine, chlorine, bromine and iodine with fluorine and chlorine being preferred.

To prepare the compounds of formula I where $R_4'$=H, $R_4$=H, and the double bond is present, X is —C— and where $R_1$ and $R_2$ do not form a benzene ring, a compound of the formula

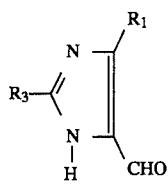
II is coupled with a compound of the formula

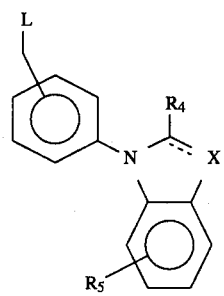
III wherein L is a leaving group such as a halogen, in the presence of a coupling agent, e.g., potassium hexamethyldisilazane, in solvents such as tetrahydrofuran and dimethylformamide, to provide the compound

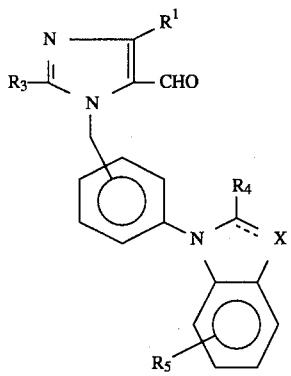
IV

Aldehyde IV can thereafter be treated with a reducing agent, such as sodium borohydride, in a solvent such as ethanol to provide

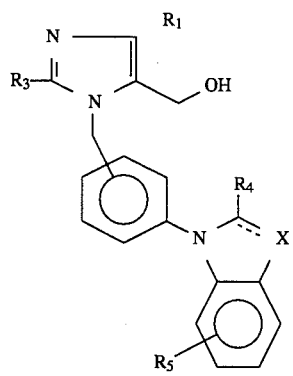
Ia that is, compounds of formula I wherein $R_2$ is —CH$_2$—OH. Using known techniques, compounds of formula I where $R_2$ is other than —CH$_2$OH can be prepared from compound Ia. For example, alcohols of formula Ia can be alkylated or acylated to provide the corresponding products of formula I. Alternatively, compounds of formula I can be prepared from IV by Wittig homologation of the aldehyde. In the methodology above, the $R_4$ and $R_5$ groups are typically H or an ester and can be converted to desired $R_4$/$R_5$ group using known techniques.

The imidazole aldehyde II can be prepared by treating a compound of the formula

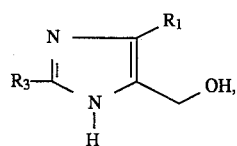
V in pyridine, with an oxidizing agent, e.g., manganese oxide.

Compounds of formula III can be prepared by coupling a compound of the formula

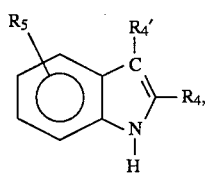
VI with a compound of the formula

VII where X is halo, e.g., bromine, for example, in pyridine and in the presence of copper oxide, to provide compounds of the formula

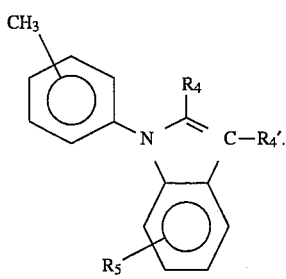

VIII

A leaving group, L, for example a halogen such as bromide, can be added by known methodology to provide compounds of the formula

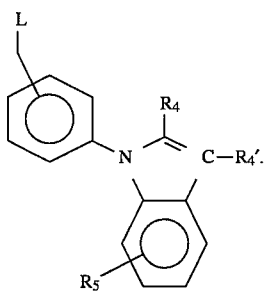

III

Compounds of formula VI can be prepared by known techniques such as those described in *J. Heterocyclic Chem.*, 25, 1 (1988).

Compounds of formula I where X is nitrogen can be prepared by reacting a compound of the formula

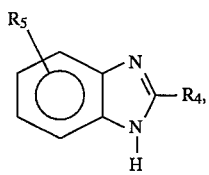

IX prepared as described by Mathias et al., *Synthetic Communications*, 5, 461–469 (1975), with a compound of the formula

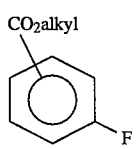

X in the presence of a base, e.g., potassium carbonate, and in a solvent, e.g., dimethylformamide, to provide a compound of the formula

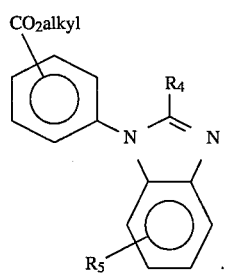

XI

Compound XI can thereafter be treated with a reducing agent, e.g., lithium borohydride, in a solvent, e.g., methanol, to provide the compound of the formula

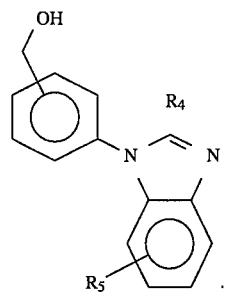

XII

Intermediates corresponding to formula III but where X=N can be prepared from compounds of formula XII and the resulting intermediates are thereafter coupled with the formula II aldehydes and then treated with a reducing agent to provide products of formula I where X is nitrogen.

A preferred method for preparing the benzimidazole (X=N) compounds of formula I where $R_4$ is tetrazolyl involves first substituting a compound of the formula

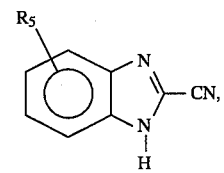

IXa for the compound of formula IX in the above methodology. (The preparation of compounds of formula IXa has been described in *Rocz. Chem.*, 51, 1783 (1977).) Thereafter, the product is treated with $Bu_3SnNa_3$ in a solvent, e.g., xylene, to convert the —CN to the desired tetrazolyl $R_4$ group. As would be understood by those skilled in the art, this methodology is also readily applicable to the preparation of the indole derivatives above wherein $R_4$ or $R_5$ can be tetrazolyl.

The compounds of formula I wherein $R_1$ and $R_2$ together with the imidazole nucleus to which they are attached form a benzimidazole can be prepared using the methodology in U.S. Pat. No. 4,880,804.

Preferred compounds of the present invention are those wherein $R_1$ is hydrogen or halogen;

$R_2$ is —CH$_2$OH or —CHO;

$R_3$ is $C_{2-10}$alkyl or $C_{3-10}$alkenyl;

$R_4$ is H or —COOH;

$R_4'$ is H or —COOH;

$R_5$ is 4-tetrazole or 4—COOH; and,

X is —CR$_4'$- or —N—.

Most preferred are compounds of formula I wherein $R_1$ is chloro;

$R_2$ is —CH$_2$OH;

$R_3$ is n-butyl;

connection from the imidazole portion is via the para-position of the benzene ring;

X is —CR$_4'$—N—; double bond is present;

$R_4$ is H;

$R_4'$ is H; and $R_5$ is 4-tetrazole.

The present compounds of formula I inhibit the action of the hormone angiotensin II (A-II) and are therefore useful, for example, as antihypertensive agents.

The action of the enzyme renin on angiotensinogen, a pseudoglobulin in blood plasma, produces angiotensin I. Angiotensin I is converted by angiotensin converting enzyme (ACE) to angiotensin II. The latter is an active pressor substance which has been implicated as the causative agent in several forms of hypertension in various mammalian species, e.g., humans. The compounds of this invention inhibit the action of A-II at its receptors on target cells and thus prevent the increase in blood pressure produced by this hormone-receptor interaction. Thus by the administration of a composition containing one (or a combination) of the compounds of this invention, angiotensin dependent hypertension in a species of mammal (e.g., humans) suffering therefrom is alleviated. A single dose, or preferably two to four divided daily doses, provided on a basis of about 0.1 to 100 mg per kilogram of body weight per day, preferably about 1 to 15 mg per kilogram of body weight per day is appropriate to reduce blood pressure. The substance is preferably administered orally, but intranasal, transdermal and parenteral routes such as the subcutaneous, intramuscular, intravenous or intraperitoneal routes can also be employed. The compounds of this invention are also useful in the treatment of congestive heart failure and cardiac hypertrophy.

The compounds of this invention can also be formulated in combination with a diuretic for the treatment of hypertension. A combination product comprising a compound of this invention and a diuretic can be administered in an effective amount which comprises a total daily dosage of about 30 to 600 mg, preferably about 30 to 330 mg of a compound of this invention, and about 15 to 300 mg, preferably about 15 to 200 mg of the diuretic, to a mammalian species in need thereof. Exemplary of the diuretics contemplated for use in combination with a compound of this invention are the thiazide diuretics, e.g., chlorthiazide, hydrochlorthiazide, flumethiazide, hydroflumethiazide, bendroflumethiazide, methylchlothiazide, trichlormethiazide, polythiazide or benzthiazide as well as ethacrynic acid, ticrynafen, chlorthalidone, furosemide, musolimine, bumetanide, triamterene, amiloride and spironolactone and salts of such compounds.

The compounds of formula I can be formulated for use in the reduction of blood pressure in compositions such as tablets, capsules or elixirs for oral administration, in sterile solutions or suspensions for parenteral or intranasal administration, or in transdermal patches. About 10 to 500 mg of a compound of formula I is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The present invention can be further illustrated by the following examples.

EXAMPLE 1

1-[4-[[2-Butyl-5-(hydroxymethyl)-1H-imidazol-1-yl]methyl]phenyl]-1 H-indole-7-carboxylic acid, monolithium salt A. 3-Methyl-2-nitrobenzoic acid, methyl ester 3-Methyl-2-nitro-benzoic acid (18.1 g, 0.1 mol) was partially dissolved in an ether and ethyl acetate mixture containing a small amount of methanol. The mixture was cooled to 0° C. and treated with an excess of a solution of diazomethane in ether. The cooling bath was removed and the mixture was stirred fifteen minutes. The solvent was removed in vacuo leaving the title A methyl ester as a white solid (19.7 g) which was used without purification in the next step.

B. 3-[2-[2-(Aminocarbonyl)hydrazono]ethyl]-2-nitrobenzoic acid, methyl ester

The title A compound (9.76 g, 50 mmol, 1.0 eq.), N,N-dimethylformamide dimethyl acetal (8.0 ml, 60 mmol, 1.2 eq.) and pyrrolidine (5.0 ml, 60 mmol, 1.2 eq.) were dissolved in dimethylformamide (28 ml, 1.8M). The solution was heated in an oil bath and maintained at 110° C. for six hours. The mixture was cooled in an ice bath and a solution of semicarbazide hydrochloride (5.86 g, 52.5 mmol, 1.05 eq.) and concentrated hydrochloric acid (4.6 ml, 55 mmol, 1.1 eq.) in water (62 ml, 0.8M) was added dropwise while stirring. The mixture was stirred at room temperature for 30 minutes and recooled to 0° C. The solid product was harvested by filtration, washed with cold water (100 ml), cold ethanol (50 ml) and ether (90 ml). The remaining material was dried in vacuo to give the title B product (6.56 g).

C. 1H-Indole-7-carboxylic acid, methyl ester

The title B semicarbazone (6.53 g, 23.3 mmol) was suspended in ethanol (50 ml), treated with 10% palladium on carbon (1.3 g, 20% by weight) and hydrogenated on a Parr shaker at up to 55 psi for six hours. The catalyst was removed by filtration through regenerated cellulose and the filtrate was dried in vacuo. The remaining material was purified by chromatography on silica gel eluting with chloroform:hexane (1:4 followed by 1:3) to give the title C compound (2.30 g) as white crystalline material.

D. 1-(4-Methylphenyl)-1H-indole-7-carboxylic acid, methyl ester

The title C indole (1.001 g, 5.713 mmol, 1.0 eq.) was dissolved in pyridine (11.4 ml, 0.5M) and treated with 4-bromotoluene (1.76 ml, 22.85 mmol, 4 eq.) and copper(I) oxide (1.635 g, 11.43 mmol, 2.0 eq.). The mixture was heated in a bath maintained at 130°±5° C. for a total of nine hours. During this period, at 3, 5.5 and 7.5 hours, additional 4-bromotoluene (0.44 ml, 5.71 mmol, 1 eq.) and copper(I) oxide (409 mg, 2.85 mmol, 0.5 eq.) were added. After cooling, the mixture was diluted with ethyl acetate (~10 ml) and filtered through Celite. The filtrate was washed with water (3×50 ml), 0.5N hydrochloric acid (2×50 ml), 1.0N hydrochloric acid (50 ml) and saturated sodium hydrogen carbonate solution. The organic solution was dried over anhydrous magnesium sulfate and freed of solvent in vacuo. The remaining material was first chromatographed on silica gel, eluting with 5% ether in hexane to give a mixture of the desired product and starting material but free of the large amount of excess 4-bromotoluene. The mixture was then rechromatographed on silica gel, eluting with 3% acetone in hexane to give the title D compound (467 mg).

E. 3-Bromo-1-[4-(bromomethyl)phenyl]-1H-indole-7-carboxylic acid, methyl ester

The title D compound (234 mg, 0.88 mmol, 1.0 eq.) was dissolved in carbon tetrachloride (8.8 ml, 0.1M) under an argon atmosphere and treated with N-bromosuccinimide (337 mg, 2.11 mmol, 2.4 eq.) and azobisisobutyronitrile (4.7 mg, 2% by weight). The mixture was heated in a bath maintained at 90°±5° C. for 12 hours. After cooling in an ice bath, the solid was removed by filtration and washed with cold carbon tetrachloride. The filtrate was freed of solvent in vacuo. The remaining material was combined with that from a smaller run (0.1168 mmol scale) and chromatographed on silica gel, eluting with toluene:hexane (1:1 followed by 2:1)

to give the title E compound (448 mg) which was a mixture of the dibromo compound along with some tribrominated material.

F. Pentanimidic acid ethyl ester hydrochloride

Hydrogen chloride gas was bubbled into a tared solution of valeronitrile (92.0 g, 1.08 mole) in absolute ethanol (64 ml, 1.08 mole) in a 1-liter round bottom flask cooled to 0° C. The flask was weighed periodically and hydrogen chloride gas bubbling was continued until the weight gain was greater than 39 g (1.08 mole). The mixture was then stoppered and stored at 0° C. for 6 days. Ether (650 ml) was then added (cold) and the mixture was stored at −30° C. for 24 hours. The resulting solid was collected on a buchner funnel, transferred quickly to a large beaker, triturated quickly with cold ether, and collected again on a buchner funnel. The solid was then dried in vacuum to give the title F compound as a free flowing white solid (95 g).

G. 2-Butyl-4-(hydroxymethyl)-imidazole

A 300 ml stainless steel Parr pressure bomb containing dihydroxyacetone dimer (5.0 g, 55 mmol) was cooled in a dry ice bath for one hour. During the cooling period, the bomb lid was set on top of the bomb and held in place by applying a light vacuum; the associated hardware for holding the lid in place under pressure was not cooled (to facilitate handling later). When the bomb was sufficiently cooled, liquid ammonia was condensed into a 250 ml three neck flask fitted with a dry ice condenser at −78° C. The cold bomb was then opened by releasing the vacuum, the title F compound (9.1 g, 55 mmol) was added, followed immediately by liquid ammonia from the 250 ml flask (approx. 55 ml of ammonia were added). The bomb was sealed using the appropriate hardware, removed from the dry ice bath, and allowed to warm to room temperature. The bomb was then immersed about half way in an oil bath and heated to 75° C. for three hours, during which the pressure rose to 320 psi. Heating was then discontinued and the bomb was allowed to cool to room temperature. When the pressure dropped below 100 psi, the pressure relief valve was slowly opened and the ammonia was allowed to evaporate (evaporative cooling helped cool the bomb). When the pressure was completely equilibrated, the bomb was opened and its contents were transferred to a conventional flask using acetonitrile to wash the residue out. The mixture was concentrated in vacuo and the residue was purified by flash chromatography on silica gel (1500 g), eluting with 80:20:1 chloroform:methanol:ammonium hydroxide. Fractions containing the major product ($R_f$ 0.5) were combined and concentrated. The residue was then crystallized from acetonitrile (200 ml) to give a white crystalline solid (5.74 g), m.p. 92°–93° C., which is 2-butyl-4-(hydroxymethyl)-imidazole, i.e., the title G compound.

H. 2-Butyl-4-formyl imidazole

The title G compound (3.0 g, 19.5 mmol, 1.0 eq.) was dissolved in pyridine (100 ml, 0.2M) and heated to 100° C. Manganese (IV) oxide (20 g, 230 mmol, 11.8 eq.) was added and the reaction was stirred for 1 hour at 100° C. The reaction was then filtered and concentrated. The residue was triturated from ether to give the title H compound (2.0 g), m.p. 113.5°–114.5° C.

I. 3-Bromo-1-[4-[(2-butyl-5-formyl-1H-imidazol-1-yl)methyl]phenyl]- 1H-indole-7-carboxylic acid, methyl ester The title E compound (404 mg, 0.954 mmol, 1.0 eq.) and the title H compound (131 mg, 0.859 mmol, 0.9 eq.) were dissolved in dimethylformamide (4.7 ml, 0.2M) in an argon atmosphere and treated with potassium t-butoxide (146 mg, 1.19 mmol, 1.25 eq.) and 18-crown-6 (0.19 mmol, 0.2 eq.). The mixture was left stirring 18 hours at room temperature, then quenched with saturated ammonium chloride solution. The products were extracted into ethyl acetate (3×50 ml), dried over anhydrous magnesium sulfate and freed of solvent in vacuo. The remaining material was chromatographed on silica gel, eluting with toluene:acetone (12:1 followed by 10:1) to give the title i compound (59 mg). Also obtained was the undesired alkylation product 3-bromo-1-[4-[(2-butyl-4-formyl-1H-imidazol-1-yl)methyl]phenyl]-1H-indole-7-carboxylic acid, methyl ester (70 mg).

J. 3-Bromo-1-[4-[[2-butyl-5-(hydroxymethyl)-1H-imidazol-1-yl)methyl]phenyl]-1H-indole-7-carboxylic acid, methyl ester The title I compound (69 mg, 0.139 mmol, 1.0 eq.) was dissolved in ethanol (1.4 ml, 0.1M) and treated with sodium borohydride (5.2 mg, 0.139 mmol, 1.0 eq.). The reaction appeared complete by TLC after 40 minutes. At 1.5 hours, 1N hydrochloric acid was added to pH 5 and the mixture was stirred 10 minutes. Most of the ethanol was removed in vacuo, water was added and the product was extracted into ethyl acetate (3×10 ml), dried over anhydrous magnesium sulfate and freed of solvent in vacuo leaving the title J compound (72 mg).

K. 1-[4-[[2-Butyl-5-(hydroxymethyl)-1H-imidazol-1-yl)methyl]phenyl]- 1H-indole-7-carboxylic acid, methyl ester The title J compound (0.139 mmol) was dissolved in methanol (2.8 ml, 0.05M) and treated with palladium hydroxide on carbon (14 mg, 20% by weight) and triethylamine (58 μl, 0.417 mmol, 3.0 eq.). The mixture was stirred under one atmosphere of hydrogen for 45 minutes. At this time HPLC indicated no starting material remained. The catalyst was removed by filtration through regenerated cellulose and the filtrate was taken to dryness in vacuo. The remaining material was chromatographed on silica gel, eluting less polar impurities with 2% methanol in dichloromethane containing 0.15% ammonium hydroxide. The desired product was then eluted with 5% methanol in dichloromethane containing 0.15% ammonium hydroxide to give the title K compound (48.1 mg).

L. 1-[4-[[2-Butyl-5-(hydroxymethyl)-1H-imidazol-1-yl]methyl]phenyl]- 1H-indole-7-carboxylic acid, monolithium salt The title K compound (48 mg, 0.115 mmol) was dissolved in methanol (1.5 ml) and treated with 1 ml of 1N lithium hydroxide solution which caused material to precipitate. The mixture was stirred at room temperature 20 hours and TLC indicated only a small amount of hydrolysis had occurred. Dioxane (1.5 ml) and saturated lithium hydroxide solution (0.5 ml) were added and the mixture was stirred at room temperature six days. The reaction was still not complete and was heated in a bath maintained at 5°±5° C. for 24 hours. The solvent was removed in vacuo. The remaining material was chromatographed on HP-20 resin (8 ml). The inorganics were removed by eluting with water and the desired lithium salt was then eluted with acetone in water (5% followed by 10%). The combined fractions containing the desired material were concentrated to a small volume in vacuo and lyophilized to give a crude product. This was dissolved in water (10 ml), passed through a polycarbonate filter and relyophilized to give the title compound (26.2 mg).

EXAMPLE 2

1-[4-[[2-Butyl-4-chloro-5-(hydroxymethyl)-1H-imidazol-1-yl]methyl] phenyl]-1H-indole-2-carboxylic acid, monopotassium salt A. 1-(4-Methylphenyl)-1H-indole-2-carboxylic acid, ethyl ester 2-Carboethoxy-indole (100 mg, 0.528 mmol, 1.0 eq.) was combined with 4-bromotoluene (0.16 ml, 1.32 mmol, 2.5 eq.) and copper(I) oxide (75.6 mg, 0.528 mmol, 1.0 eq.) in pyridine (0.53 ml, 1M) and heated at 120° C. for 2 hours. The reaction was then cooled to room temperature, diluted with ethyl acetate and filtered through celite. The filtrate was washed twice with water, twice with 1N hydrochloric acid and once with aqueous saturated sodium hydrogen carbonate, filtered through magnesium sulfate and concentrated. The residue was chromatographed on silica gel, eluting with chloroform:hexane (1:2) to give the title A compound (147.6 mg).

B. 1-[4-(Bromomethyl)phenyl]-1H-indole-2-carboxylic acid, ethyl ester

The title A compound (170.8 mg, 0.611 mmol, 1.0 eq.) was combined with N-bromosuccinimide (113.2 mg, 0.636 mmol, 1.04 eq.) and azobisisobutyronitrile (5.1 mg, 3% by weight) in carbon tetrachloride (10.2 ml, 0.06M) and heated at reflux for 2 hours. The reaction was then cooled to room temperature and concentrated. The residue was diluted with ether:hexane (1:1, 20 ml), filtered through anhydrous magnesium sulfate and concentrated. The residue was chromatographed on silica gel, eluting with ether:hexane (1:25) followed by (1:10) to give the title B compound (164.5 mg).

C. 2-Butyl-4-chloro-5-formyl imidazole

A solution of the title G compound of Example 1 ( 6.15 g, 39.9 mmol) in a mixture of absolute ethanol (40 ml) and tetrahydrofuran (80 ml) was cooled in an ice bath. To the cold solution was added N-chlorosuccinimide (5.9 g, 44.4 mmol ) in small portions over 60 minutes. The resulting mixture was stirred for 30 minutes in the ice bath, then for 30 minutes at 25° C., after which a starch-iodine test was negative. The mixture was concentrated in vacuo to give a residue which was triturated with ether (400 ml) to give a tan solid. The mother liquor from trituration was concentrated and the residue was re-triturated with ether (40 ml) to give more of the tan solid. The solids were combined, dissolved in pyridine (200 ml), and warmed to 100° C. Manganese dioxide (20 g) was added to the warm solution and the resulting black mixture was stirred at 100° C. for one hour. The hot solution was filtered and concentrated. The residue was purified by chromatography on silica gel (500 g), eluting with 3:1 hexane:ethyl acetate, to give a major product having $R_f$ 0.4. The product was triturated with petroleum ether to give the title C compound as a white crystalline solid (3.9 g), m.p. 96°–97° C.

D. 1-[4-[(2-Butyl-4-chloro-5-formyl-1H-imidazol-1-yl)methyl]phenyl]- 1H-indole-2-carboxylic acid, ethyl ester Potassium hexamethyldisilylazide (0.92 ml, 0.645 mmol, 1.4 eq., 0.7M in toluene) was added to the title C compound (120.4 mg, 0.645 mmol, 1.4 eq.) in tetrahydrofuran (1.15 ml, 0.56M) and dimethylformamide (0.38 ml, 1.7M) at 0° C. The reaction was then warmed to room temperature and stirred for 15 minutes. Next, the reaction was cooled to 0° C. and the title B compound (164 mg, 0.461 mmol, 1.0 eq.) was added in tetrahydrofuran (1.0 ml, 0.46M). The mixture was warmed to room temperature, stirred for 2 days, quenched with aqueous saturated ammonium chloride, and extracted three times with ethyl acetate. The organic extracts were filtered through magnesium sulfate and concentrated. The residue was chromatographed on silica gel, eluting with toluene: ethyl acetate (12:1) followed by (8:1) followed by (4:1) to give the title D product (127 mg).

E. 1-[4-[(2-Butyl-4-chloro-5-formyl-1H-imidazol-1-yl)methyl] phenyl]-1H-indole-2-carboxylic acid, monopotassium salt The title D compound (104.2 mg, 0,225 mmol, 1.0 eq.) was dissolved in aqueous 1N potassium hydroxide (1.0 ml, 0.22M), methanol (3.0 ml, 0.075M) and dioxane (1.0 ml, 0.22M), and stirred at room temperature overnight. Additional aqueous 1N potassium hydroxide (1.0 ml, 0.22M) was added and the reaction was stirred for 6 hours more. The mixture was then concentrated. The residue was chromatographed on HP-20 resin (10 g) eluting with water (100 ml), 2% acetone in water (100 ml), 5% acetone in water (100 ml), 10% acetone in water (100 ml) and 20% acetone in water (100 ml). The product eluted between 10% and 20%. The fractions were concentrated to a volume of ~25 ml and lyophilized to furnish the title E product (115.7 mg).

F. 1-[4-[[2-Butyl-4-chloro-5-(hydroxymethyl)-1H-imidazol-1-yl] methyl]phenyl]-1H-indole-2-carboxylic acid The title E compound (64.7 mg, 0,136 mmol, 1.0 eq.) was dissolved in ethanol (1.36 ml, 0.1M) and treated at room temperature with sodium borohydride (5.2 mg, 0.136 mmol, 1.0 eq.) dissolved in ethanol (1.36 ml). The reaction was stirred at room temperature for 90 minutes, quenched with 1N hydrochloric acid and concentrated. Water was added to the residue and the aqueous mixture was extracted three times with ethyl acetate. The organic extracts were dried over sodium sulfate, filtered through magnesium sulfate and concentrated. The residue was chromatographed on silica gel, eluting with chloroform:methanol:acetic acid (30:1.5:0.05) to give the title F product (47.1 mg).

G. 1-[4-[[2-Butyl-4-chloro-5M-(hydroxymethyl)-1H-imidazol-1-yl] methyl]phenyl]-1H-indole-2-carboxylic acid, monopotassium salt The title F compound (43 mg, 0.0982 mmol, 1.0 eq.) was dissolved in methanol (2.0 ml, 0.05M) and aqueous 1N potassium hydroxide (0.196 ml, 0.196 mmol, 2.0 eq.). After 30 minutes at room temperature, the reaction was concentrated. The residue was chromatographed on HP-20 resin (5 g) eluting with water, 5% acetone in water, 10% acetone in water, and 20% acetone in water. The fractions were concentrated to a volume of ~25 ml and lyophilized to give crude product. This was dissolved in water (10 ml) and ethanol (1 ml), filtered through a polycarbonate membrane and lyophilized to furnish the title compound (33.2 mg).

EXAMPLE 3

1-[4-[[2-Butyl-4-chloro-5-(hydroxymethyl)-1H-imidazol-1-yl]methyl] phenyl]-1H-indole-3-carboxylic acid, monolithium salt A. 1H-Indole-3-carboxylic acid, methyl ester Indole-3-carboxylic acid (757 mg, 4.7 mmol, 1.0 eq.) was partially dissolved in a mixture of ether, ethyl acetate and methanol. While stirring, a solution of diazomethane in ether was added until a yellow color persisted. The solvent was removed in vacuo and the remaining white solid was passed through a silica gel column, eluting with dichloromethane to give the title A compound (819 mg), m.p. 147°–149° C.

B. 1-(4-Methylphenyl)-1H-indole-3-carboxylic acid, methyl ester

The title A indole (819 mg, 4.67 mmol, 1.0 eq.) and 4-bromotoluene (1.44 ml, 11.69 mmol, 2.5 eq.) were dissolved in pyridine (4.7 ml, 1M) in an argon atmosphere. Copper(I) oxide (668 mg, 4.67 mmol, 1.0 eq.) was added and heated at 130°±5° C. for 8.5 hours. Ethyl acetate was added and the solid was removed by filtration through celite. The filtrate was washed with water (3×40 ml), 0.5N hydrochloric acid (2×50 ml) and saturated sodium hydrogen carbonate solution (40 ml), dried over anhydrous magnesium sulfate and freed of solvent in vacuo. The remaining brown oil was chromatographed on silica gel, eluting with 10% ether in hexane to give the title B compound (1.165 g).

C. 1-[4-(Bromomethyl)phenyl]-1H-indole-3-carboxylic acid, methyl ester

The title B compound (1.160 g, 4.37 mmol, 1.0 eq.) was dissolved in carbon tetrachloride (43 ml, 1.0M) and treated with N-bromosuccinimide (802 mg, 4.5 mmol, 1.03 eq.) and azobisisobutyronitrile (23 mg, 2% by weight). The mixture was heated in an oil bath maintained at 90°–100° C. for four hours. After cooling to 0° C., the solid was removed by filtration. The filtrate was taken to dryness in vacuo and the remaining material was chromatographed on silica gel. A small amount of starting material was eluted with 10% ether in hexane. The product was then eluted with 15% ether in hexane, followed by 30% ether in hexane and finally dichloromethane to give the title C product (1.288 g).

D. 1-[4-[(2-Butyl-4-chloro-5-formyl-1H-imidazol-1-yl)methyl] phenyl]-1H-indole-3-carboxylic acid, methylester The title C compound from EXAMPLE 2 (129 mg, 0.69 mmol, 1.15 eq.) was dissolved in distilled tetrahydrofuran (1.44 ml) and dimethylformamide (0.44 mg) (conc. 0.3M). The solution was cooled in an ice bath and potassium hexamethyldisilazide in toluene (0.7N, 1.03 ml, 0.72 mmol, 1.2 eq.) was added dropwise. The cooling bath was removed and the mixture was stirred at room temperature for 20 minutes. The mixture was again cooled to 0° C. and a solution of the title C compound (207 mg, 0.6 mmol, 1.0 eq.) in tetrahydrofuran (1 ml) was added. The mixture was left stirring at room temperature overnight. The reaction was quenched with saturated ammonium chloride solution. The product was extracted into ethyl acetate (3×30 ml), dried over anhydrous magnesium sulfate and freed of solvent in vacuo. The material remaining was chromatographed on silica gel, eluting with toluene:acetone (15:1) to give the title D compound (176 mg).

E. 1-[4-[[2-Butyl-4-chloro-5-(hydroxymethyl)-1H-imidazol-1-yl]methyl] phenyl]-1H-indole-3-carboxylic acid, methyl ester The title D product (176 mg, 0.39 mmol, 1.0 eq.) was dissolved in ethanol (3.9 ml, 0.1M), treated with a solution of sodium borohydride (14.8 mg, 0.39 mmol, 1.0 eq.) in ethanol (1 ml), and stirred at room temperature 1.5 hours. The mixture was acidified with 1N hydrochloric acid solution, stirred 30 minutes and then neutralized with solid sodium hydrogen carbonate. The product was extracted into ethyl acetate (3×20 ml), dried over anhydrous magnesium sulfate and freed of solvent in vacuo. The remaining material was chromatographed on silica gel, eluting with ether:hexane (2:1) followed by ether to give the title E compound (147 mg).

F. 1-[4-[[2-Butyl-4-chloro-5-(hydroxymethyl)-1H-imidazol-1-yl]methyl] phenyl]-1H-indole-3-carboxylic acid, monolithium salt The title E compound (147 mg, 0.325 mmol, 1.0 eq.) was suspended in methanol (3.0 ml) and 1N lithium hydroxide solution (1.5 ml). The mixture was stirred overnight at room temperature. TLC indicated little reaction had taken place. Dioxane (3 ml) was added and the mixture was stirred at room temperature for four days. The solvents were removed in vacuo. The residue was dissolved in water and chromatographed on HP-20 (30 ml), eluting with water (200 ml), 5% acetone in water (100 ml), 10% acetone in water (100 ml), 15% acetone in water (100 ml) and 20% acetone in water (100 ml). Fractions eluted with 15 and 20% acetone contained the product. These were combined and concentrated in vacuo to a small volume (due to foaming a large portion of the material was lost). This solution was lyophilized and used to obtain NMR spectra, recovered, dissolved in water, passed through a polycarbonate membrane and relyophilized to give the title compound (40 mg).

EXAMPLE 4

2-Butyl-4-chloro-1-[[4-[2-(2H-tetrazol-5-yl)-1H-indol-1-yl]phenyl]methyl]-1H-imidazole-5-carboxylic acid, dilithium salt A. 1H-Indole-2-carboxamide Indole-2-carboxylic acid (10.26 g, 63.7 mmol) was dissolved in dichloromethane (125 mL) and oxalyl chloride (39.8 mL of a 2.0M solution in methylene chloride) was slowly added dropwise to the reaction at room temperature. Upon full addition, dimethylformamide (0.32 mL) was added and the reaction was stirred for two hours. After two hours, the reaction solution was transparent yellow in color. Ammonia gas was then bubbled into the reaction for 25 minutes and the reaction was stirred at room temperature for an additional 30 minutes. The reaction was then partitioned between water and ethyl acetate. The organic phase was washed with saturated ammonium chloride, then dried and concentrated to provide crude amide (9.53 g), which was used in the next step without further purification.

B. 1H-Indole-2-carbonitrile

The title A compound (8.5 g, 53.1 mmol) was suspended in 1,4 dioxane (110 mL) and pyridine (10.74 mL). The solution was then cooled to less than 10° C. and trifluoroacetic anhydride (11.99 mL, 84.9 mmol) was slowly added to the reaction. Upon full addition, the reaction was stirred at room temperature for 18 hours. The reaction was then slowly quenched with water and extracted with ethyl acetate and the organic phase was dried and concentrated. The crude solid was purified by flash chromatography (silicon dioxide, 95:5 hexane:ethyl acetate) to provide pure nitrile (4.16 g, over 2 steps).

C. 4-(2-Cyano-1H-indol-1-yl)benzoic acid, ethyl ester

The title B compound (4.15 g, 29.2 mmol) and freshly ground potassium carbonate (8.1 g, 58.4 mmol) were placed in anhydrous dimethylformamide (60 mL). Ethyl-4-fluorobenzoate (14.73 g, 87.6 mmol) was then added via syringe at room temperature and the reaction was then heated to 110° C. for 40 hours. The reaction was then partitioned between ethyl acetate and saturated ammonium chloride and the organic phase was dried and concentrated. The crude ester was purified by flash chromatography (silicon dioxide, 96:4 Hexane:ethyl acetate) to provide pure ester (5.17 g).

1-[4-(Hydroxymethyl)phenyl]-1H-indole-2-carbonitrile

Lithium aluminum hydride (61.0 mL of 1.0M solution in ethyl ether) was added to silica gel (22.0 g) that had been vacuum dried at 150° C. for 1.5 hours and cooled to room temperature under vacuum. Ethyl ether (60 mL) was then added and the reaction was stirred at room temperature for 1.25 hours. The reaction was then cooled to −15° C. and the title C compound was added. The reaction gradually warmed to −5° C. and was stirred at this temperature for one hour. TLC indicated some starting material was still present. The reaction was then warmed to 5° C. for 1.5 hours and the reaction was found to be complete. The reaction was then cooled to 0° C. and slowly quenched with saturated ammonium chloride. The reaction was then diluted in ethyl acetate and 1N hydrochloric acid and filtered, washing the residue thoroughly with ethyl acetate. The organic filtrate was separated, dried and concentrated and the crude oil was purified by flash chromatography (silicon dioxide, 80:20 hexane:acetone) to provide pure alcohol (1.65 g).

E. 1-[4-(Bromomethyl)phenyl]-1H-indole-2-carbonitrile

The title D compound (1.92 g, 7.73 mmol) was dissolved in dry methylene chloride (38 mL) and carbon tetrabromide (2.82 g, 8.5 mmol) was added at room temperature. The reaction was then cooled to 0° C. and triphenylphosphine (2.43 g, 9.28 mmol) was added all at once. The reaction was stirred at 0° C. for five minutes, then gradually warmed to room temperature. The reaction was then concentrated and purified by flash chromatography (silicon dioxide, 95:5 hexane:acetone) to provide pure bromide (2.15 g).

F. 2-Butyl-4-chloro-1-[[4-(2-cyano-1H-indol-1-yl)phenyl]methyl]-1H-imidazole-5

The imidazole from part C of EXAMPLE 2 (0.564 g, 3.02 mmol), finely ground cesium carbonate (1.47 g, 4.5 mmol) and the bromide of part E above (0,940 g, 3.02 mmol) were combined in 30 mL of anhydrous dimethylformamide and the reaction was stirred at room temperature for 20 hours. The reaction was then partitioned between ethyl acetate and saturated ammonium chloride and the organic phase was dried and concentrated. The crude nitrile was purified by flash chromatography (SiO$_2$, 97:3 toluene:ethyl ether) to provide 1.05 g of purified title F nitrile. $^{13}$C NMR (67.8 MHz, CDCl$_3$); $_1$H NMR (270 MHz, CDCl$_3$).

G. 2-Butyl-4-chloro-1-[[4-(2-cyano-1H-indol-1-yl)phenyl]methyl]- 1H-imidazole-5-carboxylic acid The title F aldehyde (0.880 g, 2.11 mmol) and sulfamic acid (0.513 g, 5.82 mmol) were combined in 7.0 mL of anhydrous tetrahydrofuran and the reaction was cooled to 0° C. A solution of sodium chlorite (0.478 g, 5.28 mmol) in 5.3 mL of water was then slowly dropped into the reaction, keeping the temperature at 0° C. The reaction was stirred at 0° C. for 0.5 hours, then was quenched with water and extracted with methylene chloride. The organic phase was dried and concentrated to provide 0.913 g of the desired title G acid. $^{13}$C NMR (67.8 MHz, CDCl$_3$); 1H NMR (270 MHz, CDCl$_3$).

H. 2-Butyl-4-chloro-1-[[4-[2-(2H-tetrazol-5-yl)-1H-indol-1-yl] phenyl]methyl]-1H-imidazole-5-carboxylic acid, dilithium salt The title G nitrile (0.200 g, 0.462 mmol) and tributyltin azide (0.613 g, 1.85 mmol) were dissolved in 1.0 mL of anhydrous xylene and the reaction was heated to 100° C. for 20 hours. The reaction was then concentrated and the crude oil was purified by flash chromatography (SiO$_2$, 51:45:4 hexane:ethyl acetate:acetic acid) to provide 0.168 g of the desired tetrazole. 1.0M Lithium hydroxide (0.8 mL, 0.8 mmol) was added to the purified tetrazole and 5.0 mL of water was added in order to effect a solution. The solution was then placed on an HP-20 column and eluted with 250 mL of water and then 150 mL each of 2.5–15% acetone:water in 2.5% increments. The product was collected, passed through a millipore filter and lyophilized to provide 121 mg of the title compound as a pure white solid, m.p. >270° C.; $^{13}$C NMR (67.7 MHz, CD$_3$OD); $^1$H NMR (270 MHz, CD$_3$OD). Analysis calc'd for C$_{24}$H$_{20}$N$_7$ClO$_2$.2Li.3.64H$_2$O: C, 52.08; H, 4.97; N, 17.72; Cl, 6.41; Found: C, 52.53; H, 4.73; N, 17.27; Cl, 6.04.

EXAMPLE 5

2-Butyl-4-chloro-1-[[4-[2-(2H-tetrazol-5-yl)-1H-indol-1-yl]phenyl]methyl]-1H-imidazole-5-methanol, monolithium salt A. 2-Butyl-4-chloro-1-[[4-(2-cyano-1H-indol-1-yl)phenyl]methyl]- 1H-imidazole-5-carboxaldehyde The bromide of part E of EXAMPLE 4 (0.604 g, 1.94 mmol) and the imidazole of part C of Example 2 (0.398 g, 2.14 mmol) were dissolved in t-butanol (4.0 mL) and dimethylformamide (4.0 mL). Potassium t-butoxide (0.261 g, 2.3 mmol) was then added at room temperature and the reaction was heated for two hours at 60° C. The reaction was then cooled to room temperature and partitioned between ethyl acetate and water and the organic phase was washed with brine, dried and concentrated. The crude product was purified by flash chromatography (SiO$_2$, 70:30 hexane:ethyl ether) to provide 0.35 g of pure title A product. $^{13}$C NMR (67.7 MHz, CDCl$_3$); $^1$H NMR (269.6 MHz, CDCl$_3$).

B. 2-Butyl-4-chloro-1-[[4-(2-cyano-1H-indol-1-yl)phenyl]methyl]- 1H-imidazole-5-methanol The title A aldehyde (0.369 g, 0.885 mmol) was dissolved in absolute ethanol (2.0 mL) and cooled to 0° C. Sodium borohydride (0.034 g, 0.885 mmol) was added and the reaction was gradually warmed to room temperature. The reaction solution was then made pH=4 by a dropwise addition of 1N HCl. The reaction was concentrated, partitioned between ethyl acetate and saturated sodium bicarbonate and the organic phase was dried and concentrated. The crude material was purified by flash chromatography (70:30 ethyl ether:hexane) to provide 0.314 g of pure title B product. $^{13}$C NMR (67.8 MHz, CDCl$_3$); $^1$H NMR (270 MHz, CDCl$_3$).

C. 2-Butyl-4-chloro-1-[[4-[2-(2H-tetrazol-5-yl)-1H-indol-1-yl]phenyl]methyl]-1H-imidazole-5-methanol, monolithium salt The title B nitrile (0.263 g, 0.692 mmol) and tributyltin azide (0.835 g, 2.52 mmol) were dissolved in toluene (1.1 mL) and heated to 70° C. for 56 hours. The reaction was then concentrated and the crude oil was purified by flash chromatography (SiO$_2$, 92.5:7:0.05 methylene chloride:methanol:acetic acid) to provide 0.280 g of purified tetrazole. This material was dissolved in 1.0M lithium hydroxide (1.1 mL) and chromatographed through an HP-20 column eluting with 0–30% acetone:water in 5% increments (150 mL each). The fractions containing the product were filtered through a millipore filter and lyophilized to provide 0.122 g of the title product. $^{13}$C NMR (67.8 MHz, CDCl$_3$); $^1$H NMR (270 MHz, CDCl$_3$).

Analysis calc'd for C$_{24}$H$_{23}$ClN$_7$O.Li.2.9H$_2$O: C, 55.41; H, 5.58; N, 18.85; Cl, 6.82; Found: C, 55.70; H, 5.62; N, 18.56; Cl, 7.01.

EXAMPLE 6

2-Butyl-4-chloro- 1-[[4-[2 -'(2H-tetrazol-5-yl)-1 H-indol-1-yl]phenyl]methyl]-1H-imidazole-5-carboxylic acid, ethyl ester, monolithium salt A. 2-Butyl-4-chloro-1-[[4-(2-cyano-1H-indol-1-yl)phenyl]methyl]- 1H-imidazole-5-carboxylic acid, ethyl ester The acid of part F of EXAMPLE 4 (0.225 g, 0.52 mmol) and finely ground cesium carbonate (0.423 g, 1.3 mmol) were combined in 5.0 mL of anhydrous dimethylformamide. Ethyl iodide (0.162 g, 1.04 mmol) was then added and the reaction was stirred at room temperature for 110 minutes. The reaction was partitioned between ethyl acetate and saturated ammonium chloride and the organic phase was dried and concentrated to provide 0.222 g of the desired title A ester. $^{13}$C NMR (67.7 MHz, CDCl$_3$); $^1$H NMR (269.6 MHz, CDCl$_3$).

B. 2-Butyl-4-chloro-1-[[4-[2-(2H-tetrazol-5-yl)-1H-indol-1-yl]phenyl]methyl]-1H-imidazole-5-carboxylic acid, ethyl ester The title A nitrile (0.220 g, 0.48 mmol) and tributyltin azide (0.634 g, 1.90 mmol) were combined in 1.0 mL of anhydrous xylene and the reaction was heated to 100° C. for 23 hours. The solvent was then removed in vacuo and 2.0 mL of methanol was added and reaction stirred for 1 hour. The reaction was then concentrated and the crude oil was preabsorbed on silica gel and was purified by flash chromatography (SiO$_2$; 90:5:5 toluene:acetone:acetic acid) to provide 160 mg of pure title B tetrazole. $^{13}$C NMR (67.7 MHz, CD$_3$OD); $^1$H NMR (269.6 MHz, CD$_3$OD.

C. 2-Butyl-4-chloro-1-[[4-[2-(2H-tetrazol-5-yl)-1H-indol-1-yl]phenyl] methyl]-1H-imidazole-5-carboxylic acid, ethyl ester, monolithium salt 0.10M Lithium carbonate (3.2 mL, 0.32 mmol) was added to the title B tetrazole (160 mg, 0.317 mmol) and 2.0 mL of methanol was added in order to effect a solution. The reaction was stirred at room temperature for 20 minutes and then the methanol was removed in vacuo. The remaining solution was placed on an HP-20 column and eluted with 200 mL of water and then 100 mL each of 5–45% acetone:water in 5% increments. The product fractions were combined, filtered through a millipore filter and lyophilized to provide 125 mg of the desired title product, m.p. 190°–200° C.; $^{13}$C NMR (67.7 MHz, CD$_3$OD); 1H NMR (269.6 MHz, CD$_3$OD).

Analysis calc'd for C$_{26}$H$_{25}$N$_7$ClO$_2$.Li.2.2H$_2$O: C, 56.82; H, 5.39; N, 17.84; Cl, 6.45; Found: C, 57.21; H, 5.36; N, 17.17; Cl, 6.51;

EXAMPLE 7

2-Butyl-4-chloro-1-[[4-[7-(2H-tetrazol-5-yl)1H-indol-1-yl]phenyl] methyl]-1H-imidazole-5-methanol, monolithium salt A. 3-Methyl-2-nitrobenzamide Oxalyl chloride (18.1 ml, 36.1 mmol, 1.25 eq., 2M in CH$_2$Cl$_2$) was added to a solution of 2-nitro-3-methyl-benzoic acid (5.237 g, 28.9 mmol, 1.0 eq.) in CH$_2$Cl$_2$ (57.8 ml, 0.5M) and dimethylformamide (0.14 ml, 0.25% of CH$_2$Cl$_2$) at 0° C. and stirred for 15 minutes. The reaction was then warmed to room temperature and stirred for 3 hours. Ammonia was bubbled through the reaction for 30 minutes. Water was then added. The product was filtered off, and pumped on to provide the title A compound (3.81 g).

B. 3-Methyl-2-nitrobenzonitrile

Trifluoroacetic anhydride (1.72 ml, 12.2 mmol, 1.1 eq.) was added to a solution of the title A compound (1.99 g, 11.1 mmol, 1.0 eq.) in pyridine (1.79 ml, 22.1 mmol, 2.0 eq.) and dioxane (22 ml, 0.5M) at 0° C. After the addition was complete, the reaction was warmed to room temperature for 2.5 hours. More pyridine (0.54 ml, 0.6 eq.) and trifluoroacetic acid (0.47 ml, 0.3 eq.) was then added. After 30 minutes the reaction was concentrated. 1N HCl was added and the reaction was extracted three times with ether. The organic extracts were dried over Na$_2$SO$_4$, filtered through MgSO$_4$ and concentrated. The residue was chromatographed on silica gel (50 g) eluting with chloroform:hexane (2:1) to provide the title B compound (1.66 g).

C. 2-[2-(3-Cyano-2-nitrophenyl)ethylidene]-hydrazinecarboxamide

The title B compound (1.66 g, 10.3 mmol, 1.0 eq. ) was combined with (CH$_3$)$_2$NCH(OCH$_3$)$_2$ (2.05 ml, 15.4 mmol, 1.5 eq.), dimethylformamide (5.7 ml, 1.8M ) and pyrrolidine ( 1.03 ml, 12.3 mmol, 1.2 eq.) and heated at 110° C. for 4 hours. The reaction was cooled to room temperature and a solution of semicarbazide hydrochloride (1.20 g, 0.8 mmol, 1.05 eq. ) in water (12.8 ml, 0.8M) and concentrated HCl (0.93 ml, 11.3 mmol, 1.1 eq.) was added dropwise. After 45 minutes, the reaction was cooled to 0° C. The solid was filtered off, washed with cold water (10 ml), cold ethanol (10 ml) and ether (10 ml), and pumped on to give the title C compound (1.74 g).

D. 1H-Indole-7-carbonitrile

TiCl$_3$ (18.0 ml, 36.7 mmol, 7.0 eq., 20% aqueous solution) was added to the title C compound (1.296 g, 5.24 mmol, 1.0 eq.) in ethanol 5.15 ml, 0.5M) and aqueous 4N ammonium acetate at room temperature. After 10 minutes, water (20 ml) was added and the reaction was extracted with ether (3×50 ml). The organic extracts were dried over Na$_2$SO$_4$, filtered through MgSO$_4$ and concentrated. The residue was combined with product from a 0.204 mmol reaction and chromatographed on silica gel (20 g) eluting with chloroform:hexane (2:1) followed by chloroform to furnish the title D compound (586 mg).

E. 4-(7-Cyano-1H-indol-1-yl)benzoic acid, ethyl ester

The title D compound (524 mg, 3.69 mmol, 1.0 eq.) was combined with ethyl-4-fluoro-benzoic acid (0.81 ml, 5.53 mmol, 1.5 eq.), potassium carbonate (1.02 g, 7.37 mmol, 2.0 eq.) and 18-crown-6 (97.4 mg, 0.369 mmol, 0.1 eq.) in dimethylformamide (3.7 ml, 1M) and heated at 140° C. After 4 hours, more fluoride (0.81 ml, 1.5 eq.) was added. After an additional 4 hours at 150° C., the reaction was cooled to room temperature, diluted with ethyl acetate and filtered. Water was added and the mixture was extracted twice with ethyl acetate. The combined organic extracts were washed with aqueous saturated NaCl, dried over Na$_2$SO$_4$, filtered through MgSO$_4$ and concentrated. The residue was chromatographed on silica gel (50 g) eluting with chloroform:hexane (3:1) followed by (8:1) to give the title E compound (914 mg).

1-[4-(Hydroxymethyl)phenyl]-1H-indole-7-carbonitrile

Ether (12.6 ml, 0.25M) was added to a solution of the title E compound (914 mg, 3.15 mmol, 1.0 eq.) in CH$_2$Cl$_2$ (6.3 ml, 0.5M) and the reaction was cooled to 0° C. Lithium borohydride (171 mg, 7.87 mmol, 2.5 eq.) and methanol (0.32 ml, 7.87 mmol, 2.5 eq.) were added and the reaction was warmed to room temperature. After 2 hours and 4 hours, respectively, more LiBH$_4$ (85 mg, 1.25 eq.) and CH$_3$OH (0.16 ml, 1.25 eq.) were added. After a total of 5 hours, the reaction was quenched with aqueous saturated NH$_4$Cl, made acidic with 1N HCl and extracted three times with ethyl acetate. The combined organic extracts were dried over Na$_2$SO$_4$, filtered through MgSO$_4$ and concentrated. The residue was chromatographed on silica gel (40 g) eluting with chloroform:ether (5:1) followed by (2:1) to provide the title F compound (824 mg).

G. 1-[4-(Chloromethyl)phenyl]-1H-indole-7-carbonitrile

The title F compound (781 mg, 3.15 mmol, 1.0 eq.) was combined with triphenyl phosphine (1.65 g, 6.29 mmol, 2.0 eq.) in CCl$_4$ (10.5 ml, 0.3M) and heated at reflux for 90 minutes. The reaction was then cooled to room temperature, diluted with ether, filtered through MgSO$_4$ and concentrated. The residue was chromatographed on gel (40 g) eluting with chloroform:hexane (2:3) followed by (1:1) to give the title G compound (649 mg).

2-Butyl-4-chloro-1-[[4-(7-cyano-1H-indol-1-yl)phenyl]methyl]-1H-imidazole- 1-carboxaldehyde Potassium t-butoxide (352 mg, 3.04 mmol, 1.25 eq.) and 18-crown-6 (129 mg, 0.486 mmol, 0.2 eq.) were added to a solution of the title G compound (649 mg, 2.43 mmol, 1.0 eq.) and the imidazole from part C of EXAMPLE 2 (499 mg, 2.68 mmol, 1.1 eq.) in dimethylformamide (4.9 ml, 0.5M)

and stirred at room temperature overnight. In the morning, the reaction was heated at 40° C. for 2 hours. Next, the mixture was cooled to room temperature, water was added, and the reaction was extracted three times with ethyl acetate. The combined organic extracts were washed with aqueous saturated NaCl, dried over Na₂SO₄, filtered through MgSO₄ and concentrated. The residue was chromatographed on silica gel (45 g) eluting with toluene:ether (17:1) to furnish the title H compound (788 mg).

I. 2-Butyl-4-chloro-1-[[4-(7-cyano-1H-indol-1-yl)phenyl] methyl]-1H-imidazole- 1-methanol Sodium borohydride (71.5 mg, 1.89 mmol, 1.0 eq.) in ethanol (7.15 ml) was added to a solution of the title H compound (788 mg, 1.89 mmol, 1.0 eq.) in ethanol (18.9 ml, 0.1M) at room temperature. After 45 minutes, the reaction was made acidic by the dropwise addition of 1N HCl and concentrated. Aqueous saturated NaHCO₃ was added and the mixture was extracted three times with ethyl acetate. The combined organic extracts were dried over Na₂SO₄, filtered through MgSO₄ and concentrated. The residue was chromatographed on silica gel (35 g) eluting with chloroform:ether (2.5:1) to provide the title I compound (815 mg).

J. 2-Butyl-4-chloro-1-[[4-[7-(1H-tetrazol-5-yl)-1H-indol-1-yl]phenyl] methyl]-1H-imidazole-5-methanol The title I compound (773 mg, 1.84 mmol, 1.0 eq.) was combined with Bu₃SnN₃ (3.06 g, 9.23 mmol, 5.0 eq.) in xylene (3.7 ml, 0.5M) and heated at 130° C. for 17 hours. The reaction was then cooled to room temperature, diluted with chloroform:methanol:acetic acid (4:1:1, 14.8 ml), stirred at room temperature overnight and concentrated. The residue was chromatographed on silica gel (50 g) eluting with chloroform:methanol:acetic acid (30:1.5:0.05) to furnish the title J compound (418 mg).

K. 2-Butyl-4-chloro-1-[[4-[7-(2H-tetrazol-5-yl)-1H-indol-1-yl] phenyl]methyl]-1H-imidazole-5-methanol, monolithium salt Aqueous 1N LiOH (8.0 ml) was added to a solution of the title J compound (418 mg, 0.905 mmol, 1.0 eq.) in methanol (8 ml) at room temperature. After 30 minutes, the reaction was concentrated. The residue was chromatographed on HP-20 resin (20 g) eluting with water (100 ml), 5% acetone in water (200 ml), 10% (100 ml), 20% (200 ml), and 30% (200 ml). The product fractions were concentrated, dissolved in water (15 ml), filtered through a polycarbonate filter and lyophilized to furnish the title compound (298 mg).

What is claimed is:

1. A compound of the formula

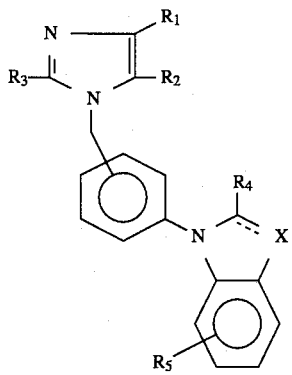

I pharmaceutically acceptable salt thereof;
where X is —N— or

when X=N, the double bond is always present;

$R_1$ is hydrogen, halogen, —NO₂, —CF₃ or —CN;

$R_2$ is H, CN, alkyl of 1 to 10 carbon atoms, alkenyl of 3 to 10 carbon atoms, or the same groups substituted with F; phenylalkenyl wherein the aliphatic portion is 2 to 6 carbon atoms; —(CH₂)$_m$-imidazol-1-yl; —(CH₂)$_m$-1,2,3-triazolyl unsubstituted or substituted with one or two groups selected from COOR₇ or alkyl of 1 to 4 carbon atoms;

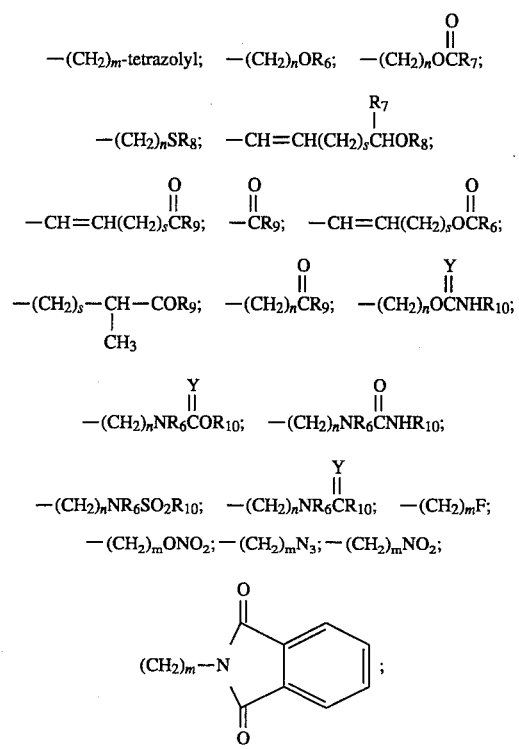

or $R_1$ and $R_2$ taken together with the carbon atoms of the imidazole nucleus to which they are attached form a benzimidazole shown as

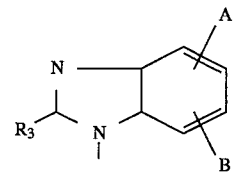

wherein A is hydrogen, alkyl, $C_xF_{2x+1}$, $C_6F_5$, halogen, $C_{1-6}$alkoxy, —(CH₂)$_x$OH, —(CH₂)$_{x—O}C_{1-4}$alkyl,

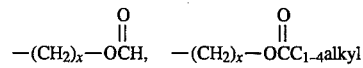

or —COR₉ and B is hydrogen, alkyl, $C_xF_{2x+1}$, $C_6F_5$, halogen or $C_{1-6}$alkoxy;

$R_3$ is alkyl of 2 to 10 carbon atoms, alkenyl or alkynyl of 3 to 10 carbon atoms or the same groups substituted with F or $CO_2R_7$; cycloalkyl of 3 to 8 carbon atoms, cycloalkylalkyl of 4 to 10 carbon atoms; cycloalkylalkenyl or cycloalkylalkynyl of 5 to 10 carbon atoms; —$(CH_2)_sZ(CH_2)_mR'$ (wherein R' is H, $C_{1-6}$alkyl, $C_{3-6}$cycloalkyl, $C_{2-4}$alkenyl or $C_{2-4}$alkynyl) unsubstituted or substituted with F or $CO_2R_7$; benzyl or benzyl substituted on the phenyl ring with 1 or 2 halogens, alkoxy of 1 to 4 carbon atoms, alkyl of 1 to 4 carbon atoms or nitro;

$R_4$ and $R_4'$ are independently selected from hydrogen, alkyl, aryl, cycloalkyl, aralkyl,

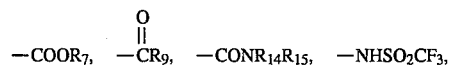

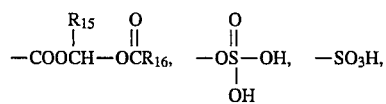

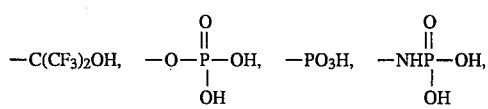

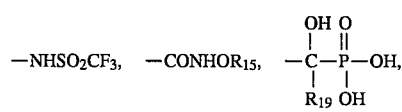

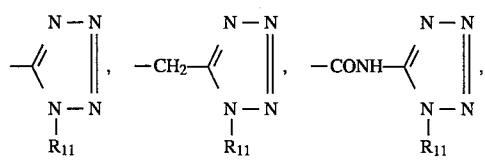

$R_5$ is hydrogen, 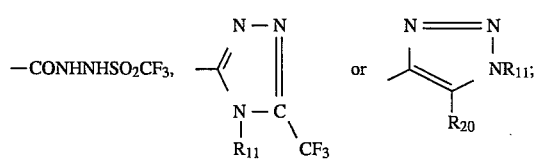

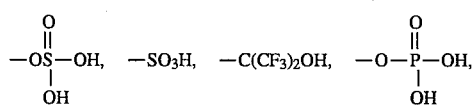

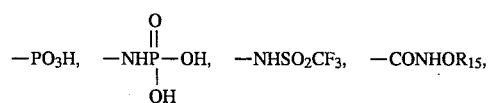

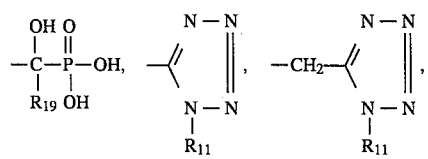

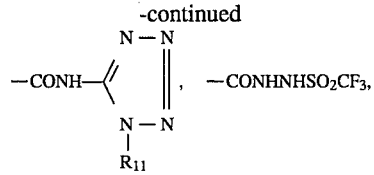

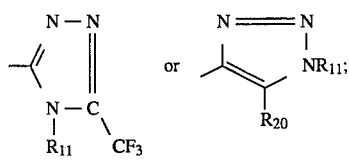

$R_6$ is H, alkyl of 1 to 6 carbon atoms, cycloalkyl of 3 to 6 carbon atoms, phenyl or benzyl;

$R_7$ is H, alkyl or perfluoroalkyl of 1 to 8 carbon atoms, cycloalkyl of 3 to 6 carbon atoms, phenyl or benzyl;

$R_8$ is H, alkyl of 1 to 6 carbon atoms, cycloalkyl of 3 to 6 carbon atoms, phenyl, benzyl, acyl of 1 to 4 carbon atoms, phenacyl;

$R_9$ is H, alkyl of 1 to 6 carbon atoms, cycloalkyl of 3 to 6 carbon atoms, $(CH_2)_pC_6H_5$, $OR_{11}$ or $NR_{12}R_{13}$;

$R_{10}$ is alkyl of 1 to 6 carbon atoms or perfluoroalkyl of 1 to 6 carbon atoms, 1-adamantyl, 1-naphthyl, 1-(1-naphthyl)ethyl, or $(CH_2)_pC_6H_5$;

$R_{11}$ is H, alkyl of 1 to 6 carbon atoms, cycloalkyl of 3 to 6 carbon atoms, aryl, arylalkyl, a 5- to 7-membered carbocyclic ring or a 5- to 7-membered carbocyclic ring having another 5- to 7-membered carbocyclic ring fused thereto,

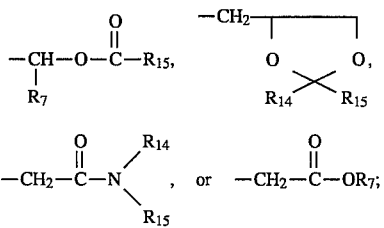

$R_{12}$ and $R_{13}$ independently are H, alkyl of 1 to 4 carbon atoms, phenyl,

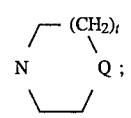

benzyl, α-methylbenzyl, or taken together form a ring of the formula

Q is $NR_{14}$, O or $CH_2$;

$R_{14}$ and $R_{15}$ are independently H, alkyl, aryl, aralkyl or cycloalkyl;

$R_{16}$ is $C_{1-6}$alkyl, —$NR_{17}R_{18}$ or

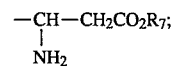

$R_{17}$ and $R_{18}$ are independently H, $C_{1-6}$alkyl, benzyl or taken together are 3 to 6 carbon atoms forming a 4- to 7-membered ring with the nitrogen atom to which they are attached;

$R_{19}$ is H, $C_{1-5}$alkyl, phenyl;

$R_{20}$ is —CN, —NO$_2$ or —CO$_2$R$_7$;

Y=O or S;

Z=O, NR$_6$ or S;

m=is 1–5;

n is 1–10;

p is 0–3;

q is 2–3;

r is 0–2;

s is 0–5;

t is 0 or 1; and x is 1 to 6.

2. A compound of claim 1 wherein $R_1$ is hydrogen or halogen;

$R_2$ is —CH$_2$OH or —CHO;

$R_3$ is $C_{2-10}$alkyl or $C_{3-10}$alkenyl;

$R_4$ is H or —COOH;

$R_4'$ is H or —COOH;

$R_5$ is 4-tetrazole or 4-COOH; and

X is —CR$_4'$— or —N—.

3. A compound of claim 1 wherein $R_1$ is chloro;

$R_2$ is —CH$_2$OH;

$R_3$ is n-butyl;

connection from the imidazole portion is via the para-position of the benzene ring;

X is —CR$_4'$;

double bond is present;

$R_4$ is H;

$R_4'$ is H; and $R_5$ is 4-tetrazole.

4. A compound of claim 1 having the name 1-[4-[[2-butyl-5-(hydroxymethy)-1H-imidazol-1-yl] methyl]phenyl]-1H-indole-7-carboxylilc acid, monolithium salt.

5. A compound of claim 1 having the name 1-[4-[[2-butyl-4-chloro-5-(hydroxymethy)-1H-imidazol-1-yl]methyl]phenyl]-1H-indole-2-carboxylic acid, monopotassium salt.

6. A compound of claim 1 having the name 1-[4-[[2-butyl-4-chloro-5-(hydroxymethy)-1H-imidazol-1-yl]methyl]phenyl]-1H-indole-3-carboxylilc acid, monolithium salt.

7. A compound of claim 1 having the name 2-butyl-4-chloro-1-[[4-[2-(2H-tetrazol-5-yl)- 1H-indol-1-yl]phenyl]methyl]-1H-imidazole-5-carboxylilc acid, dilithium salt.

8. A compound of claim 1 having the name 2-butyl-4-chloro-1-[[4-[2-(2H-tetrazol-5-yl)- 1H-indol-1-yl]phenyl]methyl]-1H-imidazole-5-methanol, monolithium salt.

9. A compound of claim 1 having the name 2-butyl-4-chloro-1-[[4-[2-(2H-tetrazol-5-yl)- 1H-indol-1-yl]phenyl]methyl]-1H-imidazole-5-carboxylilc acid, ethyl ester, monolithium salt.

10. A compound of claim 1 having the name 2-butyl-4-chloro-1-[[4-[7-(2H-tetrazol-5-yl)-1H-indol-1-yl]phenyl]methyl]-1H-imidazole-5-methanol, monolithium salt.

11. A pharmaceutical composition comprising a compound of claim 1 and a pharmaceutically acceptable carrier.

12. A method of treating hypertension comprising administering to a mammalian specie in need thereof a therapeutically effective amount of a composition of claim 11.

\* \* \* \* \*